US008568967B2

(12) United States Patent
Urade et al.

(10) Patent No.: US 8,568,967 B2
(45) Date of Patent: Oct. 29, 2013

(54) METHOD FOR DIAGNOSIS OF SEVERITY AND PREDICTION OF RECURRENCE IN EOSINOPHILIC INFLAMMATORY DISEASE

(75) Inventors: Yoshihiro Urade, Kyoto (JP); Naomi Eguchi, Suita (JP); Kosuke Aritake, Kawanishi (JP); Sawako Hyo, Kyoto (JP); Hiroshi Takenaka, Kyoto (JP); Ryo Kawata, Kyoto (JP)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 1135 days.

(21) Appl. No.: 11/920,543

(22) PCT Filed: May 17, 2006

(86) PCT No.: PCT/JP2006/309800
§ 371 (c)(1),
(2), (4) Date: Nov. 16, 2007

(87) PCT Pub. No.: WO2006/123677
PCT Pub. Date: Nov. 23, 2006

(65) Prior Publication Data
US 2010/0138937 A1    Jun. 3, 2010

(30) Foreign Application Priority Data

May 17, 2005 (JP) ................................ 2005-144432

(51) Int. Cl.
 A61K 38/43 (2006.01)
 A61K 38/00 (2006.01)
 C12Q 1/00 (2006.01)
 C12N 9/00 (2006.01)
 C12N 9/90 (2006.01)
 C07K 1/00 (2006.01)

(52) U.S. Cl.
 USPC ............. 435/4; 424/94.1; 424/94.5; 435/183; 435/233; 530/350

(58) Field of Classification Search
 None
 See application file for complete search history.

(56) References Cited

U.S. PATENT DOCUMENTS 7,202,394 B1    4/2007    Urade et al.

FOREIGN PATENT DOCUMENTS

| EP | 1 224 861 A1 | 7/2002 |
| JP | 2002-534507 | 10/2002 |
| WO | 00/42019 | 7/2000 |
| WO | 01/24627 | 4/2001 |
| WO | 2004/016223 | 2/2004 |
| WO | 2004/031180 | 4/2004 |
| WO | 2004/078719 | 9/2004 |

OTHER PUBLICATIONS

Chica et al. Curr Opin Biotechnol. Aug. 2005;16(4):378-84.*
Nihon•meneki•gakkai General assembly, scientific meeting record (0919-1984), vol. 34, p. 106 (Nov. 2004), with abridged English translation.
Ziten, 48:3; 199-206, 2005, with full English translation.
Supplementary European Search Report issued Feb. 24, 2009 in European Application No. 06746503.9.
J. Knani et al., "Indirect Evidence of Nasal Inflammation Assessed by Titration of Inflammatory Mediators and Enumeration of Cells in Nasal Secretions of Patients with Chronic Rhinitis", J. Allergy Clin. Immunol., (Dec. 1992), vol. 90, No. 6, pp. 880-889.
F. Nantel et al., "Expression of Prostaglandin D Synthase and the Prostaglandin $D_2$ Receptors DP and CRTH2 in Human Nasal Mucosa", Prostaglandins and Other Lipid Mediators, (Jan. 1, 2004), vol. 73, No. 1-2, pp. 87-101.
C. Rudack et al., "Chronic Rhinosinusitis—Need for Further Classification", Inflammation Research, (2004), vol. 53, pp. 111-117.
R. Jankowski et al., "Clinical Factors Influencing the Eosinophil Infiltration of Nasal Polyps", Rhinology, (Jan. 1, 2002), vol. 40, No. 4, pp. 173-178.
S. Hyo et al., "Expression of Prostaglandin $D_2$ Synthase in Activated Eosinophils in Nasal Polyps", Archives of Otolaryngology—Head & Neck Surgery, (Jul. 7, 2007), vol. 133, No. 7, pp. 693-700.
M. Okano et al., "Role of Prostaglandin $D_2$ and $E_2$ Terminal Synthases in Chronic Rhinosinusitis", Clinical and Experimental Allergy, (Aug. 1, 2006), vol. 36, pp. 1028-1038.
International Search Report issued Jul. 4, 2006 in the International (PCT) Application of which the present application in the U.S. National Stage.
European Office Action issued Oct. 14, 2010 in corresponding European Application No. 06 746 503.9.
European Office Action issued Mar. 30, 2011 in corresponding European Application No. 06 746 503.9.
Rothenberg ME. Eosinophilic gastrointestinal disorders (EGID). J Allergy Clin Immunol. Jan. 2004;113(1):11-28.
Picus D, Frank PH. Eosinophilic esophagitis. AJR Am J Roentgenol. May 1981;136(5):1001-3.
Japanese Office Action issued Dec. 13, 2011 in corresponding Japanese Patent Application No. 2007-516307 (with English translation).
Matsumoto, R. et al., "Involvement of expression of synthetase in chronic (eosinophilic) sinusitis with clinical condition of PGD2", Allergy, 2005, Apr. 30, 2005, vol. 54, No. 3/4, p. 384 (with English translation).
Japanese Office Action issued Jul. 12, 2011 in corresponding Japanese Application No. 2007-516307.
Sawako Hyo et al., "Involvement of hematopoietic prostaglandin D2 synthase (HPGDS) with nasal polyp of chronic sinusitis", Nihon Jibi Inko-Ka Gakkai Kaiho, 2005, vol. 108 No. 4, p. 456.
Mitsuhiro Okano, et al., "Involvement of prostaglandin synthase with development of refractory sinusitis", Nippon Jibiinkoka Gakkai Kaiho, 2005, vol. 108, No. 4, p. 455.
Japanese Office Action issued Jul. 12, 2011, in corresponding Japanese Application No. 2007-516307.
Hyo S et al., "Involvement of hematopoietic prostaglandin D2 synthase (HPGDS) with nasal polyp of chronic sinusitis", Nippon Jibiinkoka Gakkai Kaiho, Apr. 20, 2005, vol. 108, No. 4, p. 456.
Okano M et al., "Involvement of prostaglandin synthase with development of refractory sinusitis", Nippon Jibiinkoka Gakkai Kaiho, Apr. 20, 2005, vol. 108, No. 4, p. 455.

* cited by examiner

Primary Examiner — Christian Fronda
(74) Attorney, Agent, or Firm — Wenderoth, Lind & Ponack, L.L.P.

(57) ABSTRACT

A method is provided for diagnosis of the severity of a condition in an eosinophilic inflammatory disease such as nasal polyp and for prediction of the recurrence of the disease.

10 Claims, 6 Drawing Sheets

Fig. 5

METHOD FOR DIAGNOSIS OF SEVERITY AND PREDICTION OF RECURRENCE IN EOSINOPHILIC INFLAMMATORY DISEASE

This application is a U.S. national stage of International Application No. PCT/JP2006/309800 filed May 17, 2006.

TECHNICAL FIELD

The present invention relates to a method for diagnosis of severity in eosinophilic inflammation diseases whereby recurrence of those diseases is predicted. More particularly, the present invention relates to that where activation of eosinophils accumulated at the inflammatory sites by diseases such as chronic sinusitis (particularly chronic sinusitis associated with nasal polyp), allergic rhinitis, bronchial asthma (particularly, allergic bronchial asthma) and allergic dermatitis is measured by an expressed amount of hematopoietic prostaglandin D synthase (H-PGDS) gene or protein in eosinophils as an index whereby severity of those eosinophilic inflammatory diseases is diagnosed and recurrence thereof is predicted.

BACKGROUND OF THE INVENTION

Although it has not been clarified yet how nasal polyp is formed, it was formerly thought that inflammation by infection participated in its origin because it is an inflammatory lesion which is perceived being associated with chronic sinusitis. On the other hand, when nasal polyp is histologically observed, many of it is associated with eosinophilic infiltration and, therefore, its origin has been also presumed to be participation of eosinophilic inflammation such as bronchial asthma and allergic rhinitis.

Nasal polyp induces not only nasal obstruction and heavy feeling of the head among the symptoms of chronic sinusitis but also makes the sinusitis severe due to ventilatory disorder of paranasal sinus and disorder of lower respiratory tract due to postnasal drip.

Accordingly, although the treatment of chronic sinusitis accompanied by nasal polyp is an surgical therapy, recurrence is noted within two to three years in the case where asthma is complicated therewith or in the case where local eosinophilic infiltration is severe.

When patients suffering from allergic rhinitis represented by hay fever or from allergic bronchial asthma are exposed to antigen, chemical mediators such as prostaglandin (PG)$D_2$, $PGE_2$, histamine and leukotriene (LT)$C_4$, $LTD_4$ and $LTE_4$ are excessively produced and released from mast cells and then inflammatory cells represented by eosinophils are locally accumulated. When the accumulated eosinophils are activated, they are thought to release tissue-injuring proteins such as major basic protein (MBP) and eosinophilic cationic protein (ECP) and they make the inflammation more serious.

Prostaglandin D2 ($PGD_2$) has been known to be involved in diseases such as chronic sinusitis (nasal polyp), allergic rhinitis, bronchial asthma (particularly allergic bronchial asthma) and allergic dermatitis (e.g. Non-Patent Documents 1 and 2). On the other hand, amount of $PGE_2$, $LTC_4$, $LTD_4$ and $LTE_4$ and infiltration numbers of eosinophils have been used as indexes for severity in those diseases. However, to date diagnosis on severity of those diseases and their prediction recurrence by evaluating the expression of hematopoietic prostaglandin D synthase (H-PGDS) protein in the inflammatory sites has been reported.

Administration of steroids (glucocorticoids) shows a significant effect for the treatment of those diseases but, in view of their side effects, chronic administration is limited. Although administration of nonsteroidal anti-inflammatory drugs, antiallergic agents, antihistaminic agents or anti-leukotriene agents is presently in practice, variation on their effect among individuals is large.

Non-Patent Document 1: Allergy, Vol. 54, No. 3/4, Page 384
Non-Patent Document 2: Allergy, Vol. 52, No. 8/9, Page 759

Problems that the Invention is to Solve

The objective of the present invention is to provide a method for diagnosis of severity of eosinophilic inflammatory diseases and for prediction of recurrence of those diseases in which expression of hematopoietic prostaglandin D synthase (H-PGDS) protein is monitored.

SUMMARY OF THE INVENTION

In order to achieve the above object, the present inventors have carried out intensive studies and achieved the present invention based on the following findings.

1) In severe nasal polyp as a result of sinusitis, infiltration of eosinophils is significant.

2) H-PGDS is not normally expressed in eosinophils. However, in lesion sites, its expression is promoted in EG2- or MBP-positive activated eosinophils.

3) The amount of H-PGDS expression in eosinophils is correlated to severity of eosinophilic inflammatory diseases. Thus, the higher is the expression of H-PGDS, the more severe is the eosinophilic inflammatory disease.

4) The amount of H-PGDS expression in eosinophils is correlated to recurrence rate of nasal polyp. Thus, the higher is expression of H-PGDS, the more is the recurrence rate of nasal polyp.

Accordingly, the present invention is a method for diagnosis of severity of eosinophilic inflammatory diseases where its gist is a method for the diagnosis of severity comprising the measurement of the amount of hematopoietic prostaglandin D synthase (H-PGDS) protein expression or the measurement of the amount of prostaglandin $D_2$ ($PGD_2$) in the inflammatory site.

The present invention also relates to a method for the prediction of recurrence of eosinophilic inflammatory disease where its gist is a method for the prediction of recurrence comprising the measurement of the amount of hematopoietic prostaglandin D synthase (H-PGDS) protein expression or the measurement of the amount of prostaglandin $D_2$ ($PGD_2$) in the inflammatory site.

Another gist of the present invention is a screening method for compounds used for prevention of the progression of eosinophilic inflammatory disease or prevention for the recurrence comprising the followings that 1) The mice overexpressing human H-PGDS is sensitized by antigen to prepare an allergic disease model and the mouse is challenged by antigen to nasal cavity, airway or skin to induce an eosinophilic allergic disease, 2) a candidate compound of an inhibitor for hematopoietic prostaglandin D synthase (H-PGDS) or of prostaglandin receptor (DP) antagonist is administered to the transgenic mouse before or after induction of eosinophilic disease and 3) the state of eosinophilic inflammatory disease in the transgenic mouse is compared with the state of a transgenic mouse to which no candidate compound was administered.

Effect of the Invention

In accordance with the present invention, a novel diagnostic method for severity of eosinophilic inflammatory diseases and a method for prediction of recurrence of those diseases are able to be provided. Moreover, in accordance with the present invention, it is possible to prevent the progress of eosinophilic inflammatory diseases and to screen a compound which is used for prevention of recurrence.

DETAILED DESCRIPTION OF THE PREFERRED EMBODIMENTS

The eosinophilic disease which is an object of the present invention comprises chronic sinusitis (particularly chronic sinusitis associated with nasal polyp), allergic rhinitis, bronchial asthma (particularly, allergic bronchial asthma) or allergic dermatitis.

In the present invention, "severity" means an index for classifying the eosinophilic inflammatory diseases into mild, medium and severe states and is diagnosed according to diagnostic standard or severity classification (such as "Guidelines for Diagnosis of Nasal Allergy", Edition of 2002, prepared by Allergy Rhinitis Guideline Group, Enterprise for Development, Promotion and Study of Medicine [EBM Field] of the 21st Century Type, Ministry of Welfare and Labor) for each disease.

In the present invention, "recurrence" means recrudescence of symptom of eosinophilic inflammatory disease (particularly, nasal polyp) and, in the case of chronic sinusitis for example, the case where tumor of paranasal mucous membrane is noted within two years after excision of nasal polyp is called "recurrence".

Specimens used in the present invention are collected from inflammatory sites and, in the cases of nasal allergic rhinitis, bronchial asthma (particularly, allergic bronchial asthma), etc., nasal alveolar lavage fluid or bronchial alveolar lavege fluid may be used. For example, nasal cavity is washed with a physiological saline solution, the recovered liquid is centrifuged, the precipitate is made into a smear, the smear is stained is subjected to an H-PGDS antibody staining or a Wright-Giemsa staining and H-PGDS-positive eosinophils are identified. Amount of prostaglandin ($PGD_2$) in the supernatant prepared by centrifugation of the recovered fluid is quantified by an EIA method (refer to Krawiec M E, Westcott J Y, Chu H W, Balzar S, Trudeau J B, Schwartz L B, Wenzel S E, Persistent wheezing in very young children is associated with lower respiratory inflammation, Am. J. Respir. Crit. Care Med., 2001; 163:1338-1343 and Shichijo M, Inagagi N, Naka N, Kimata M, Nakahata T, Serizawa I, Iikura Y, Saito H, Nagai H, The effect of anti-asthma drugs on mediator release from cultured human mast cells, Clin. Exp. Allergy, 1998 October; 28(10):1228-36) or an LC-MS method (refer to Sugimoto M, Sugiyama S, Yanagita N, Ozawa T, Laser high performance liquid chromatography determination of prostaglandins in nasal lavage fluid in allergic rhinitis, Clin. Exp. Allergy, 1994 April; 24(4):324-9).

As will be illustrated in the following Examples, the expression of H-PGDS in eosinophils of inflammatory area is detected by a histochemical analysis, an RT-PCR method, Western blotting method or an in situ hybridization method. Those methods are known among persons skilled the art. Examples of application of those methods for the measurement of H-PGDS are mentioned in the following documents. Thus, Hematopoietic prostaglandin D synthase is expressed in microglia in the developing postnatal mouse brain, Glia, 2003, May, 42(3):263-74; Induction of hematopoietic prostaglandin D synthase in hyalinated necrotic muscle fibers: its implication in grouped necrosis. Neuropathol. (Berl). 2002, October, 104(4):377-84. Epub 2002 Jun. 6; Essential role for hematopoietic prostaglandin D2 synthase in the control of delayed type hypersensitivity. Proc. Natl. Acad. Sci. USA, 2006 Mar. 28; 103(13):5179-84. Epub 2006 Mar. 17. Those documents are incorporated herein for reference.

It has been clarified that the more severe is the eosinophilic inflammatory diseases, the higher is the amount of $PGD_2$ and the amount of H-PGDS protein expression in the inflammatory site of eosinophilic inflammatory disease are. Accordingly, the present invention provides a diagnostic method for eosinophilic inflammatory disease where it is diagnosed that, the higher is the amount of H-PGDS protein expression or the amount of $PGD_2$ in the inflammatory site of eosinophilic inflammatory disease collected from a patient is, the more severe is the eosinophilic inflammatory disease.

With regard to the $PGD_2$ amount and H-PGDS as measured above, it has been also clarified that the higher is the amount of $PGD_2$ and the expressed amount of H-PGDS protein in the inflammatory site of eosinophilic inflammatory disease, the higher is the recurrence of the eosinophilic inflammatory disease. It has been clarified particularly in the case of nasal polyp that the higher is the amount of $PGD_2$ and the expressed amount of H-PGDS protein in nasal polyp, the higher is the recurrence of nasal polyp, particularly the recurrence within two years when the history after excision of nasal polyp is traced. Accordingly, the present invention also provides a method of prediction of recurrence of eosinophilic inflammatory disease where it is predicted that the higher is the expressed amount of H-PGDS protein or the amount of $PGD_2$ in the inflammatory site of eosinophilic inflammatory disease collected from a patient, the higher is the recurrence of the eosinophilic inflammatory disease. It further provides a method for prediction of recurrence of nasal polyp where it is predicted that the higher is the expressed amount of H-PGDS protein or the amount of PGD$_2$ in nasal polyp collected from a patient, the higher is the recurrence of nasal polyp.

It has now become clear in accordance with the present invention that there is a correlation between eosinophilic inflammatory disease and expression of H-PGDS and, therefore, it is able to be predicted that expression of H-PGDS is a cause of onset of eosinophilic inflammatory disease. Accordingly, there is a possibility that an H-PGDS inhibiting substance or a DP antagonistic drug is able to be a treating agent for eosinophilic inflammatory disease.

Examples of the H-PGDS inhibitor include 4-benzhydryloxy-1-{3-(1H-tetrazol-5-yl)-propyl}piperidine (HQL-79), 1-amino-4-{4-[4-chloro-6-(2-sulfo-phenylamino)-[1,3,5]triazin-2-ylmethyl]-3-sulfo-phenylamino-}-9,10-dioxo-9,10-dihydroanthracene-2-sulfonic acid (Cibacron Blue), 1-amino-4-(4-sulfamoylanilino)-anthraquinone-2-sulfonic acid (PGD-042) or a pharmaceutically acceptable salt or a hydrate thereof and 2-(2'-benzothiazolyl)-5-styryl-3-(4'-phthalhydrazidyl)tetrazolium chloride (PGD-016) or a hydrate thereof.

With regard to the pharmaceutically acceptable salt, examples of basic salt are alkali metal salt such as sodium salt and potassium salt; alkali earth metal salt such as calcium salt and magnesium salt; ammonium salt; aliphatic amine salt such as trimethylamine salt, triethylamine salt, dicyclohexylamine salt, ethanolamine sat, diethanolamine salt, triethanolamine salt and procaine salt; aralkylamine salt such as N,N-dibenzoylethylenediamine salt; heterocyclic aromatic amine salt such as pyridine salt, picoline salt, quinoline salt and isoquinoline salt; quaternary ammonium salt such as tetramethylammonium salt, tetraethylammonium salt, benzyltrimethylammonium salt, benzyltriethylammonium salt, benzyltributylammonium salt, methyltrioctylammonium salt and tetrabutylammonium salt; and basic amino acid salt such as arginine salt and lysine salt. Examples of acidic salt are inorganic acid salt such as hydrochloride, sulfate, nitrate, phosphate, carbonate, bicarbonate and perchlorate; organic acid salt such as acetate, propionate, lactate, maleate, fumarate, tartrate, malate, citrate and ascorbate; sulfonate such as methanesulfonate, isethionate, benzenesulfonate and p-toluenesulfonate; and acidic amino acid salt such as aspartate and glutamate. Those salts may be produced by a commonly conducted method. When a hydrate is formed, it may be coordinated with any numbers of water molecules.

Examples of the antagonist to prostaglandin D receptor are (±)-3-benzyl-5-(6-carboxyhexyl)-1-(2-cyclohexyl-2-hydroxyethylamino)-hydantoin (BW A868C), (+)-(3R)-3-(4-fluorobenzenesulfonamide)-1,2,3,4-tetrahydrocarbazole-9-propionic acid (ramatroban), (Z)-7-[(1R,2R,3S,5S)-2-(5-hydroxybenzo[b]thiophen-3-ylcarbonylamino]-10-norpinan-3-yl]hept-5-enoic acid, (Z)-7-[(1R,2R,3S,5S)-2-(benzo[b]-thiophen-3-ylcarbonylamino)-10-norpinan-3-yl] hept-5-enoic acid (pinagladin) or a pharmaceutically acceptable salt or a hydrate thereof.

When a diagnostic method represented in the present invention is conducted and the amount of H-PGDS expression or the amount of PGD$_2$ production is measured before and after administration of the compound to a patient suffering from eosinophilic inflammatory disease, it is now possible to confirm whether said compound is a effective agent for eosinophilic inflammatory disease.

The present invention also relates to a screening method for a compound used for prevention of the progress of eosinophilic inflammatory disease or prevention for the recurrence comprising the followings that 1) The mouse overexpressing human H-PGDS is sensitized by antigen to prepare an allergic disease model and then the mouse is challenged by antigen to its nasal cavity, airway or skin to induce an eosinophilic allergic diseases, 2) a candidate compound for an H-PGDS inhibitor or a DP antagonist is administered to the transgenic mouse before or after induction of eosinophilic inflammatory disease and 3) the state of the eosinophilic inflammatory disease in the transgenic mouse is compared with the state in the transgenic mouse to which no candidate compound is administered.

According to a method disclosed in WO 01/24727, where hematopoietic prostaglandin D synthase (H-PGDS) overexpressing transgenic mouse is able to be prepared. This document is incorporated herein for reference. From a cDNA library prepared from mRNA of human cells, cDNA of rat H-PGDS gene (Cell, 90:1085-10975, 1997; GenBank Accession No. D82071) is probed so that cDNA of human H-PGDS (Eur. J. Biochem. 267:3315-3322, 2000; GenBank Accession No. NM-014485) is subjected to a cloning. After that, cDNA of human H-PGDS is inserted into and bonded to a cloning site (Sal I/Not I) of the vector pCAGGS (Gene, 108:193-199 (1991)) to construct a transducing vector. FIG. 18 is a constitution of the inserted gene in this inducing vector. This inserted gene has a CMV enhancer and a chicken β-actin promoter in the upstream region of the H-PGDS cDNA and, upon introduction into chromosomes of a mouse, H-PGDS mRNA is abundantly expressed due to the action of those enhancer and promoter. This inducing vector is injected into fertilized ovum of a mouse of an FVB strain (obtained from the National Institute of Health Animal Genetic Resource) by a microinjection method. The fertilized ovum into which the gene was introduced is transplanted to uterine tube of a host or proxy parent according to a common method, generated to individuals and given to birth. DNA is extracted from the tail of the resulting mice and transgenic mice are selected by a Southern blotting method using a probe synthesized based on the sequence of the inserted gene.

Then an eosinophilic allergic disease model is prepared using a transgenic mouse where human H-PGDS is abundantly expressed. Ovalbumin suspended in an aluminum hydroxide gel is administered (sensitized) as an antigen to a mouse intraperitoneally or intratracheally. After two to three weeks from the sensitization, the mouse is exposed by ovalbumin solution which is the antigen to nasal cavity, airway or skin to induce an eosinophilic allergic disease. In a challenged group, a significant infiltration of eosinophils in nasal cavity, airway or skin in observed after 24 to 72 hours compared with in a not challenged group.

As hereunder, examples where the present invention is conducted to chronic sinusitis will be illustrated. Those examples are with a purpose of explanation and it goes without saying that the present invention is not limited to the examples.

EXAMPLE 1

As a treatment for a patient suffering from chronic sinusitis, an excision operation of nasal polyp was conducted. For the purpose of analyzing the infiltration of the eosinophils in the excised nasal polyp, a histochemical analysis was carried out using the nasal polyp tissue. At first, the excised nasal polyp was fixed with 10% neutralized formalin and then a paraffin section was prepared. The slice was stained with hematoxylin-eosin (HE) by a conventional method and observed under a microscope to measure the numbers of eosinophils per infiltrated cell and the case where the ratios were 20% or more and 10% or less were classified as examples of high eosinophil infiltration and non-eosinophilic nasal polyp, respectively.

Figure 1:
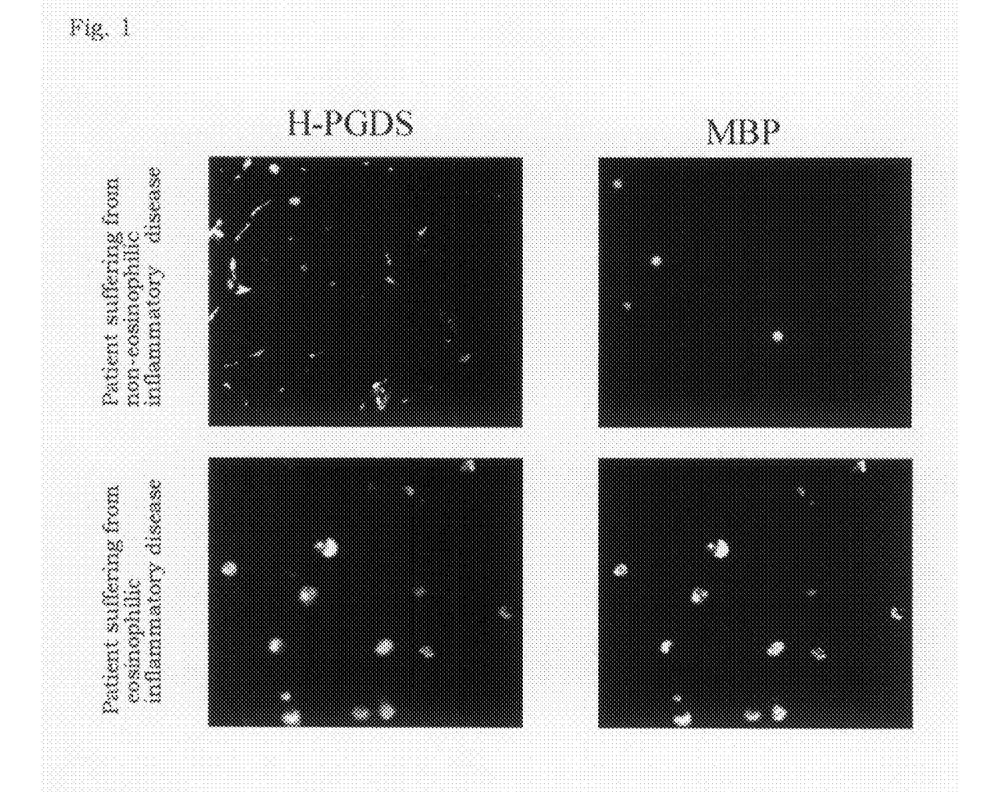
FIG. 1 shows a immunostaining of MBP (index for eosinophils) and H-PGDS. In the upper panel line for a patient suffering from non-eosinophilic disease, H-PGDS hardly coincides with MBP-positive cells while, in a patient where infiltration of eosinophils is significant, most of MBP-positive cells express H-PGDS.

Backgrounds of the patients are shown in Table 1. In nasal polyps used for the experiments, the seven cases were severe degree and the another seven cases were mild degree shown in Table 1. In seven cases among the above, specific IgE antibody against to mite was positive in peripheral blood. In terms of the rate of the peripheral eosinophils before the operation, there was no significant difference between the two groups.

hardly coincided with H-PGDS-positive cells in the tissue (L3) of a patient where infiltration of eosinophils is mild, while, in the tissue where infiltration of eosinophils was significant (H6), H-PGDS was expressed in most of MBP-positive cells (refer to FIG. 1). It was found that, when positive stained cells were compared per unit area, the rate of cells where H-PGDS protein was expressed in the MBP-positive

TABLE 1

| Samples | Age/Sex | Allergic | Eosinophils in Peripheral Blood (%) | Topically Infiltrating Eosinophils (/mm$^2$) | (EG2 + Cells)/ (MBP + Cells) (%) | (HPGDS + Cells)/ (MPB + Cells) (%) | (HPGDS + Cells)/ (EG2 + Cells) (%) |
|---|---|---|---|---|---|---|---|
| | | | | Eosinophilic | | | |
| H1 | 26/F | + | 22 | 74 | 98 | 55 | 56 |
| H2 | 76/M | − | 13.7 | 74 | 14 | 12 | 85 |
| H3 | 59/M | − | 7.2 | 61 | 54 | 35 | 64 |
| H4 | 38/M | + | 8 | 51 | 99 | 68 | 67 |
| H5 | 57/M | − | 1.7 | 46 | 92 | 72 | 79 |
| H6 | 61/M | + | 15.8 | 40 | 78 | 59 | 76 |
| H7 | 68/M | + | 2.3 | 20 | 28 | 7.5 | 27 |
| Mean ± S.D. | 55.0 ± 17.3 | | 10.1 ± 7.4 | 52.3 ± 19.4 | 65.8 ± 34.7 | 43.8 ± 26.0* | 64.8 ± 19.2* |
| | | | | Non-eosinophilic | | | |
| L1 | 23/f | − | 0.6 | 8.2 | 0.7 | 0.4 | 50 |
| L2 | 64/M | − | 0.7 | 8.1 | 35 | 8.4 | 24 |
| L3 | 34/M | + | 4.2 | 6 | 23 | 4.6 | 20 |
| L4 | 68/F | − | 1.6 | 4.9 | 13 | 1.4 | 11 |
| L5 | 38/F | − | 4.9 | 4.2 | 90 | 38 | 42 |
| L6 | 68/M | + | 5.2 | 3 | 50 | 20 | 40 |
| L7 | 50/M | + | 10.8 | 2.3 | 45 | 12 | 27 |
| Mean ± S.D. | 49.3 ± 18.1 | | 4 ± 3.6 | 5.2 ± 2.3 | 46.8 ± 29.2 | 12.1 ± 13.3 | 30.5 ± 13.8 |

Expression of H-PGDS in MBP-Positive Activated Eosinophils

For the purpose of searching the cell distribution of H-PGS in nasal polyp, an enzymatic immuno-staining was conducted using H-PGDS and an antibody to major basic protein (MBP) which is an index for eosinophils.

At first, a paraffin section of nasal polyp fixed with 10% neutralized formalin was dipped in 100% xylene to remove paraffin. After that, a reaction was carried out at room temperature for 10 minutes using a 0.3% pepsin solution to activate the antigenicity. After that, a reaction was carried out at room temperature for 1 hour in a phosphate buffer containing 10% of normal goat serum and 0.1% of Triton to mask the non-specific bonding site of the protein. Then, a reaction was carried out at 4° C. for one night with an H-PGDS antibody (polyclonal rabbit anti-human HPGDS antibody, manufactured by Cayman Chemical; diluted to an extent of 1:10,000 using a blocking solution) and an anti-MBP antibody (monoclonal anti-human eosinophil major basic protein antibody, clone BMK; purchased from Biodesign International; diluted to an extent of 1:1,000 with a blocking solution) and, after washing, a further reaction was carried out with Alexa 488 labeled anti-rabbit IgG antibody and Alexa 546 labeled anti-mouse IgG antibody (manufactured by Molecular Probes; diluted to an extent of 1:500) as the secondary antibody at room temperature for 1 hour. After a full washing, an observation was conducted by a common method (Nantel F, Fong C, Lamontague S, et al., Expression of prostaglandin D$_2$ receptors DP and CRTH2 in human nasal mucosa. Prostaglandins and Other Liquid Mediat., 2004; 73:87-101) using a confocal fluorescent microscope (Radiance 200 manufactured by Bio-Rad).

As a result, it was found that, when H-PGDS expression was compared with that of major basic protein (MBP) which was used as an index for eosinophils, MBP-positive cells cells was significantly high in the case where eosinophil infiltration was high (refer to Table 1).

EXAMPLE 2

Expression of H-PGDS in EG2-Positive Activated Eosinophils

For a purpose of investigating the distribution of H-PGDS in nasal polyp in the activated eosinophils, expression of H-PGDS and the antibody (Bentley A M, Jacobson M R, Cumberworth V, Barkans J R, Moqbel R, et al., Immunohistology of the nasal mucosa in seasonal allergic rhinitis: increases in activated eosinophils and epithelia mast cells, J. Allergy Clin. Immunol., 1992; 89(4):877-83) which specifically recognizes EG2 antigen (injury protein recognized in eosinophils activated by eosinophil cationic protein (ECP)) which is an index for activated eosinophils was compared by an immunohistochemical staining method.

At first, a paraffin section of nasal polyp fixed with 10% neutralized formalin was dipped in 100% xylene to remove paraffin and then antigenicity was activated by a 0.3% pepsin solution. After that, a blocking was carried out using a PBS containing 10% normal goat serum and 0.1% Triton X, the primary antibody was added thereto and a reaction was conducted at 4° C. for overnight. As the primary antibody, an HPGDS antibody (polyclonal rabbit anti-human HPGDS antibody; purchased from Cayman Chemical; diluted with a blocking solution to an extent of 1:10,000) or an anti-EG2 antibody (monoclonal anti-human eosinophil cationic protein antibody, clone EG2; manufactured by Pharmacia) was made to react therewith and, by the same manner as above, an immuno-staining was conducted using Alexa 488 labeled anti-rabbit IgG antibody and Alexa 546 labeled anti-mouse IgG antibody (Molecular Probes; diluted to an extent of 1:500) as the secondary antibodies and an observation was conducted under a confocal fluorescent microscope (Radiance 2000 manufactured by Bio-Rad).

Figure 2:
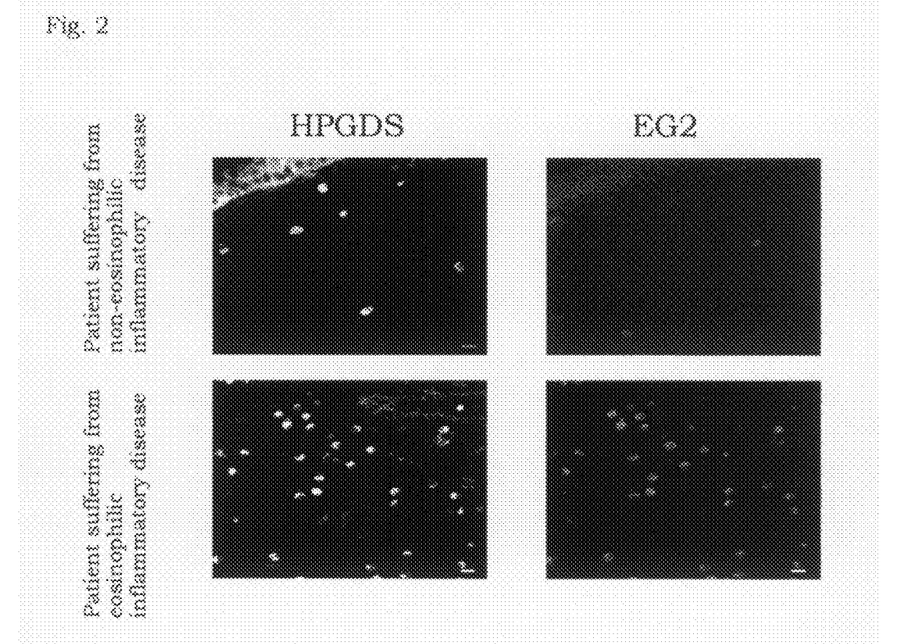
FIG. 2 shows a immunostaining of EG2 (activated eosinophil) and H-PGDS. In the upper line for a patient where eosinophil infiltration is mild, H-PGDS-positive cells hardly coincide to EG2-positive cells (activated eosinophils) while, in a patient where eosinophil infiltration is significant, most of EG2-positive cells coincide H-PGDS-positive cells. The scale is 10 p.m.

It has been found as a result that, in the tissue (L3) where infiltration of eosinophils were mild, EG2-positive cells (eosinophils) and H-PGDS-positive cells hardly coincided while, in the tissue (H6) of a patient where infiltration of eosinophils was significant, H-PGDS was expressed in most of the EG2-positive cells (refer to FIG. 2). Further, considering the ratio of H-PGDS positive cells per unit area in EG2-positive cells, the ratio is higher in the group that eosinophils infiltration is severe than in the mild (refer to Table 1).

EXAMPLE 3

Western Blotting of Nasal Polyp Tissue Specimens Collected from Patients Suffering from Chronic Sinusitis (1)

For a detection of the expression of H-PGDS protein in nasal polyp, an SDS gel electrophoresis was conducted using an extract of nasal polyp tissue and a Western blotting by using an antibody against H-PGDS was conducted. After the electrophoresis, the proteins were transferred to a nylon membrane. A western blotting was conducted by using an antibody against H-PGDS.

At first, about 50 mg of the excised specimen was homogenized in 0.5 ml of PBS, centrifuged at 7,000 g (at 4° C. for 20 minutes) and then centrifuged at 100,000 g (at 4° C. for 1 hour) to separate into a supernatant liquid and a microsome fraction. The supernatant obtained by 7,000 g centrifugation and the microsome obtained by 100,000 g centrifugation were subjected to electrophoresis to 10/20% SDS-PAGE gradient gel and 4/20% SDS-PAGE gradient gel (both manufactured by Daiichi Kagaku), respectively and transferred to a PVDF membrane (Millipore) at 100 mA for 1 hour. Non-specific bond was blocked by skim milk and made to react at 4° C. for over night with an H-PGDS antibody (polyclonal rabbit anti-human HPGDS antibody; purchased from Cayman Chemical; used by diluting to 1:5,000) and a cyclooxygenase (COX)-1 antibody (polyclonal rabbit anti-human COX-1 antibody; purchased from Cayman Chemical; used by 1:1000 dilution), and COX-2 antibody (polyclonal rabbit anti-human COX-2 antibody; purchased from Ctma Chemical; used by diluting to 1 μg/mL) after diluting with a PBS containing 5% of skim milk and 0.1% of Tween 20. After that, a reaction with an HRP labeled anti-mouse IgG antibody or an anti-rabbit IgG antibody (purchased from Jackson Laboratories; used by diluting to 1:1,000 with Tris buffer) as the secondary antibody was conducted at room temperature for 1 hour. After that, a reaction was conducted with an ECL detection reagent (manufactured by Amersham International) at room temperature for 2 minutes and exposed to Kodak XOMAT AR film (manufactured by Eastman Kodak) for 15 minutes followed by developing.

Figure 3:
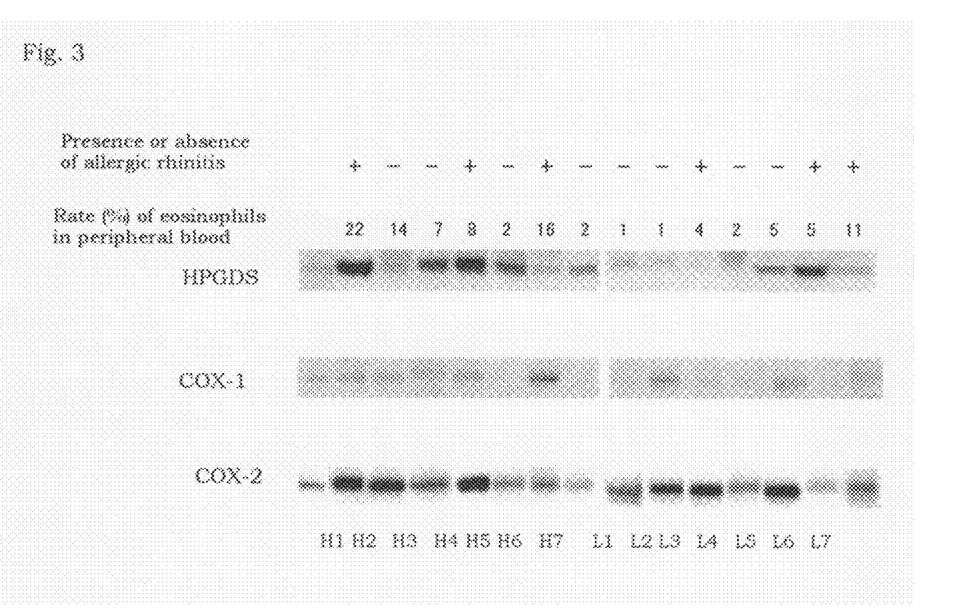
FIG. 3 shows Western blottings of H-PGDS, COX-1 and COX-2 in nasal polyps. Seven cases in the left side are patients where eosinophil infiltration was significant while seven cases in the right side are patients where eosinophil infiltration is mild.

The result was that the seven cases on the left side were a group (H1 to 7) where infiltration of eosinophils in the lesion site was significant and the seven cases on the right side were a group where infiltration of eosinophils was mild. From the left, the cases H1 to 7 and L1 to 7 are shown. Regardless of presence or absence of allergic rhinitis, expression of H-PGDS was significant in all examples in the left side (H1 to 7). A high correlation was noted between expression of H-PGDS and severity of the disease. In the right side (L1 to 7), highly expression was noted in three cases among the seven. However, no correlation was noted between expression of cyclooxygenase (COX)-1 or COX-2 and severity of the disease. Further, the rate of peripheral eosinophils was high in all of the three cases where H-PGDS expression was high in the group where eosinophil infiltration was mild whereby a relation between eosinophils and H-PGDS is predicted (refer to FIG. 3).

EXAMPLE 4

For a purpose of checking the relation between expression of H-PGDS protein and recurrence at the stage of excision of nasal polyp, clinical course after excision of the nasal polyp was traced and expression of H-PGDS was investigated in which the cases where tumor of paranasal mucosa was noted within two years were defined as a recurrent group while the cases where no tumor of the mucosa was noted within two years were defined as a group where the clinical course was good. Background of the patients is shown in Table 2.

TABLE 2

| Case Numbers | Age/Sex | Eosinophils in Peripheral Blood (%) | Allergic | Topical Infiltration of Eosinophils |
|---|---|---|---|---|
| R1 | 26/F | 22 | + | high |
| R2 | 61/M | 4 | + | high |
| R3 | 76/M | 13.7 | − | high |
| R4 | 68/M | 5.2 | − | low |
| R5 | 55/F | 26 | + | high |
| R6 | 70/M | 14 | + | high |
| R7 | 64/M | 0.7 | − | low |
| R8 | 50/M | 10.8 | − | low |
| R9 | 38/F | 4.9 | − | low |
| R10 | 34/M | 4.2 | + | low |
| R11 | 23/F | 0.6 | − | low |
| R12 | 68/F | 0.9 | − | low |
| R13 | 24/F | 4.9 | + | low |
| R14 | 65/F | 1.4 | − | low |

Western Blotting of Nasal Polyp Tissue Specimens Collected from Patients Suffering from Chronic Sinusitis (2)

A Western blotting (Kanaoka Y, Ago H, Inagaki E, et al., Cloning and crystal structure of hematopoietic prostaglandin D synthase, Cell, 1997; 90:1085-1095) was conducted by the same method as in Example 3 using H-PGDS antibody, cyclooxygenase (COX)-1 and COX-2 antibody.

Figure 4:
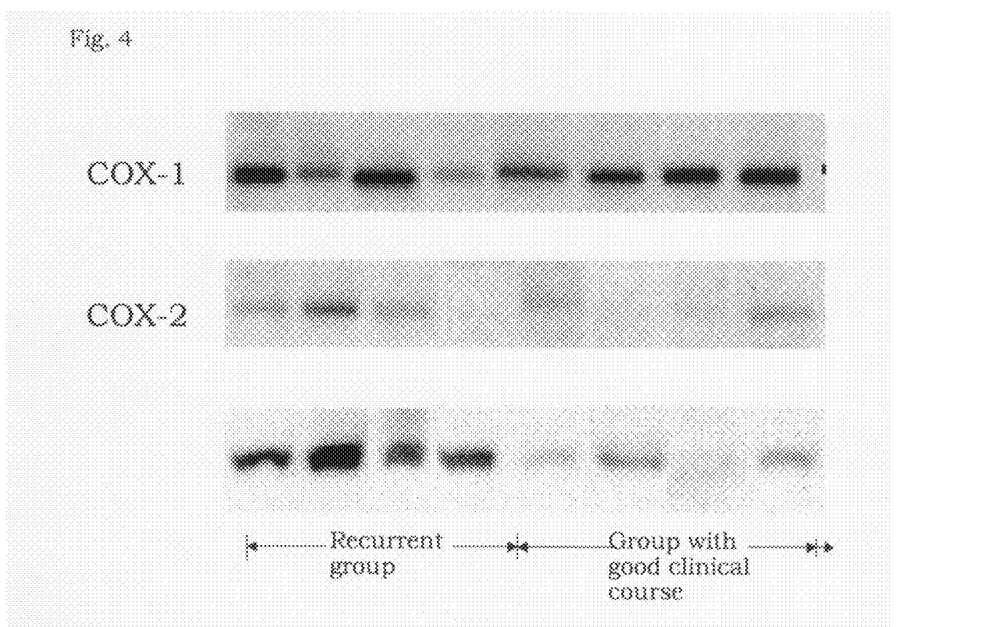
FIG. 4 shows Western blottings of H-PGDS, COX-1 and COX-2 in nasal polyps. Four cases in the left side are the cases where polyp recurred within two years from operations while four cases in the right side are the cases where the clinical course is good showing no recurrence. As compared with the cases where the clinical course is good, expression of H-PGDS is abundant in the recurred group.

The result was that, in the recurrent group (cases R1 to 4 from the left), expressed amount of H-PGDS in nasal polyp was high. On the other hand, in the cases where the clinical course was good (cases R8 to 11 from the left; a good group), expression of H-PGDS was low. Accordingly, it is possible to predict the recurrence of nasal polyp by the expressed amount of H-PGDS (refer to FIG. 4).

EXAMPLE 5

Quantitative PCR of Nasal Polyp Tissue Specimens Collected from Patients Suffering from Chronic Sinusitis For a purpose of checking the relation between expression of H-PGDS mRNA and recurrence rate, a quantitative PCR (Kanaoka Y, Ago H, Inagaki E, et al., Cloning and crystal structure of hematopoietic prostaglandin D synthase, Cell, 1997; 90:1085-1095) was carried out.

Extraction of total RNA and reverse transcription to cDNA were conducted, using RN easy Mini Kit and Omniscript RT Kit (both from Qiagen), from nasal polyp which was quickly stored by freezing at −80° C. after excision by an operation. Light Cycler-FastStart DNA Master SYBR Green 1 (Roche) was used for the quantitative PCR. Primer of H-PGDS was designed as F1:5'GAATAGAACAAGCTGACTGGC (SEQ ID NO: 1) and R1:5'AGCCAAATGTGTGTTTTTGG (SEQ ID NO: 2) and subjected to thermal denaturation at 95° C. for 10 minutes followed by conducting under the condition of 95°

C. for 15 seconds; 57° C. for 5 seconds; and 72° C. for 10 seconds for 40 cycles. As an internal standard, measurement was conducted for GAPDH gene. Primer of GAPDH was designed as F1:5'TGAACGGGAAGCTCACTGG (SEQ ID NO: 3) and R1:5'TCCACCACCCTGTTGCTGTA (SEQ ID NO: 4) and subjected to thermal denaturation at 95° C. for 10 minutes followed by conducting under the condition of 95° C. for 15 seconds; 63° C. for 20 seconds; and 72° C. for 10 seconds for 40 cycles. Quantification of cDNA was conducted by a fluorescent measuring method using Light Cycler TM System (Roche).

Figure 5:
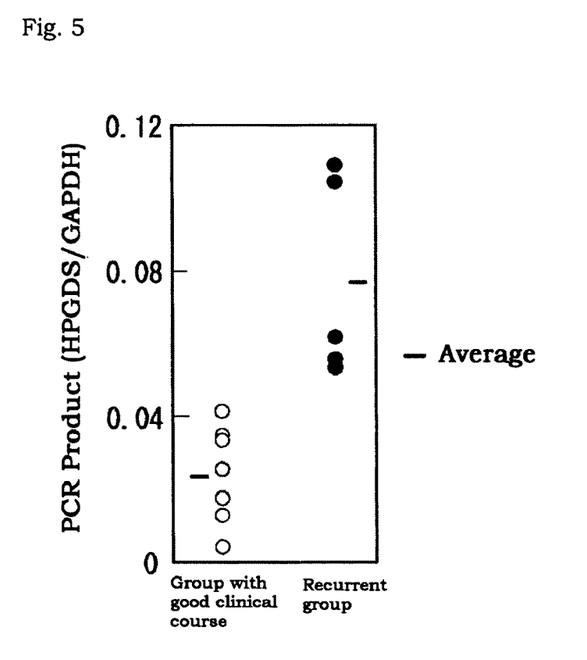
FIG. 5 shows the amount of H-PGDS mRNA expression in nasal polyp. As compared with the group where the clinical course is good, the amount of the expression is abundant in the recurred group.

The result was that, the same as in the result of H-PGDS protein, expressed amount of H-PGDS was high in nasal polyp in the cases where nasal polyp was recurred within two years. On the other hand, in the cases where clinical course was good, expression of H-PGDS was low (see to FIG. 5).

The above result shows that recurrence of nasal polyp is able to be predicted by quantification of amounts of H-PGDS protein and mRNA of the tissues collected from patients by a Western blotting method or a PCR method.

EXAMPLE 6

For a purpose of checking the relation between recurrence rate and H-PGDS expression in eosinophils, a antibody staining was conducted for eosinophilic EG2 antibody and H-PGDS by the same method as in Example 2.

Figure 6:
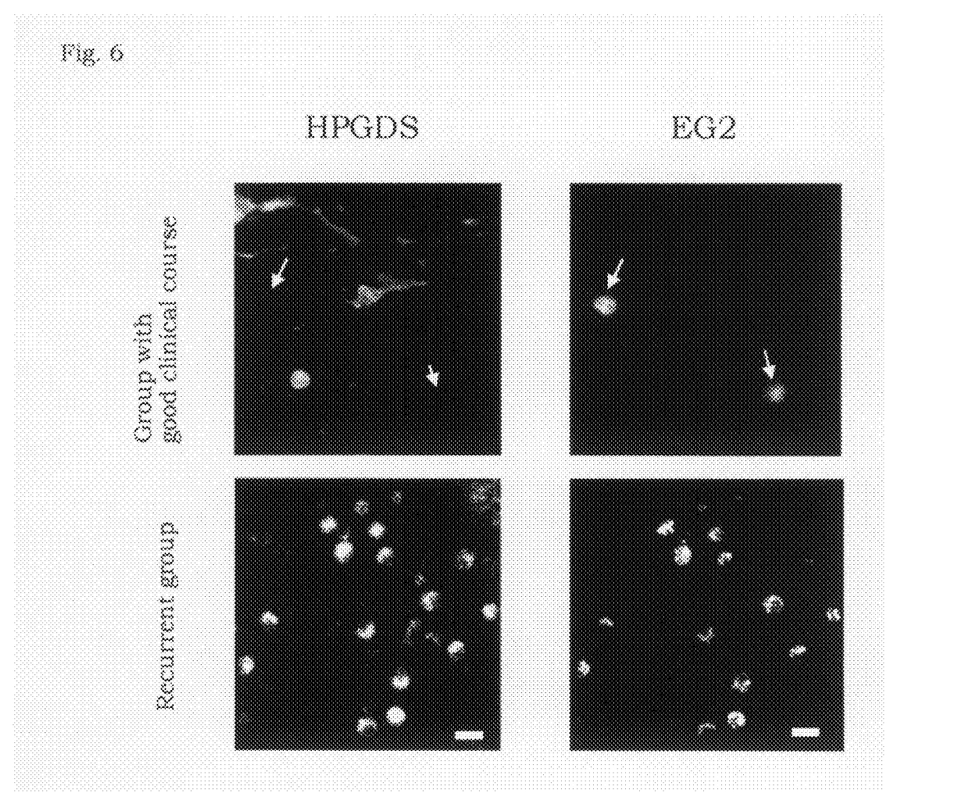
FIG. 6 shows a immunostaining of eosinophil EG2 and H-PGDS. In the recurrent group, most of the EG2-positive cells coincide H-PGDS-positive cells. The scale is 10 µm.

The result was that, in a group where the clinical course was good (case R12), H-PGDS was hardly coincident with EG2-positive cells (shown by arrows in FIG. 6) while, in a recurrent group (case R6), most of EG2-positive cells were coincident with H-PGDS-positive cells. The above result shows that the nasal polyp in which activated eosinophils are abundant where both H-PGDS and EG2 are positive shows a high recurrence rate.

INDUSTRIAL APPLICABILITY

As fully described hereinabove, the present invention provides a method in which, in eosinophilic inflammatory diseases such as nasal polyp, H-PGDS induced in eosinophils accumulated in the lesion sites is detected or $PGD_2$ in a washing of nasal cavity or in a bronchioalveolar lavage fluid is measured whereby severity of the disease is diagnosed or recurrence of the disease is predicted.

What is claimed is:

1. A method for diagnosis of the severity of eosinophilic inflammatory disease comprising the measurement of the expressed amount of hematopoietic prostaglandin D synthase (H-PGDS) protein or the measurement of the amount of prostaglandin $D_2$ ($PGD_2$) in a sample obtained from an inflammatory site in a subject, wherein the eosinophilic inflammatory disease is chronic sinusitis accompanied by nasal polyp, and wherein a higher expressed amount of hematopoietic prostaglandin D synthase (H-PGDS) or a higher amount of prostaglandin $D_2$ ($PGD_2$) correlates to more severe eosinophilic inflammatory disease.

2. A method for the prediction of recurrence of eosinophilic inflammatory disease comprising the measurement of the expressed amount of hematopoietic prostaglandin D synthase (H-PGDS) protein or the measurement of the amount of prostaglandin $D_2$ ($PGD_2$) in a sample obtained from an inflammatory site in a subject, wherein the eosinophilic inflammatory disease is chronic sinusitis accompanied by nasal polyp, and wherein a higher expressed amount of hematopoietic prostaglandin D synthase (H-PGDS) or a higher amount of prostaglandin $D_2$ ($PGD_2$) correlates to a higher predicted recurrence rate of eosinophilic inflammatory disease.

3. The method for the prediction of recurrence according to claim 2, wherein the measurement of the expressed amount of hematopoietic prostaglandin D synthase (H-PGDS) protein or the measurement of the amount of prostaglandin $D_2$ ($PGD_2$) is in eosinophils.

4. The method for the prediction of recurrence according to claim 3, wherein the eosinophils are EG2 or MBP positive eosinophils.

5. The method for the prediction of recurrence according to claim 3, wherein the eosinophils are activated eosinophils.

6. The method for the prediction of recurrence according to claim 4, wherein the eosinophils are activated eosinophils.

7. The method for diagnosis according to claim 1, wherein the measurement of the expressed amount of hematopoietic prostaglandin D synthase (H-PGDS) protein or the measurement of the amount of prostaglandin $D_2$ ($PGD_2$) is in eosinophils.

8. The method for diagnosis according to claim 7, wherein the eosinophils are EG2 or MBP positive eosinophils.

9. The method for diagnosis according to claim 7, wherein the eosinophils are activated eosinophils.

10. The method for diagnosis according to claim 8, wherein the eosinophils are activated eosinophils.

* * * * *

UNITED STATES PATENT AND TRADEMARK OFFICE
CERTIFICATE OF CORRECTION

| | | |
|---|---|---|
| PATENT NO. | : 8,568,967 B2 | Page 1 of 1 |
| APPLICATION NO. | : 11/920543 | |
| DATED | : October 29, 2013 | |
| INVENTOR(S) | : Urade et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1279 days.

Signed and Sealed this
Twenty-fourth Day of February, 2015

Michelle K. Lee
*Deputy Director of the United States Patent and Trademark Office*

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 1
gaatagaaca agctgactgg c                                          21

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 2
agccaaatgt gtgtttttgg                                            20

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence:primer

<400> SEQUENCE: 3
tgaacgggaa gctcactgg                                             19

<210> SEQ ID NO 4
<211> LENGTH: 20
<212> TYPE: DNA
<213> ORGANISM: Artificial Sequence
```

-continued

```
<220> FEATURE:
<223> OTHER INFORMATION: Description of Artificial Sequence:primer

<400> SEQUENCE: 4
tccaccaccc tgttgctgta                                              20
```